United States Patent [19]

Dombrowski

[11] Patent Number: 5,047,206

[45] Date of Patent: Sep. 10, 1991

[54] REAGENT TEST STRIP

[75] Inventor: Mitchell P. Dombrowski, Grosse Point Farms, Mich.

[73] Assignee: Wayne State University, Detroit, Mich.

[21] Appl. No.: 24,573

[22] Filed: Mar. 11, 1987

[51] Int. Cl.$^5$ ............................................ G01N 31/22
[52] U.S. Cl. ................................ 422/56; 156/73.1; 422/57; 422/58; 427/2; 436/165
[58] Field of Search .......................... 422/56, 57, 58; 436/165; 427/2; 156/73.1

[56] References Cited

U.S. PATENT DOCUMENTS

| | | | |
|---|---|---|---|
| 3,092,464 | 6/1963 | Adams, Jr. et al. | 422/56 |
| 3,690,836 | 9/1972 | Buissiere et al. | 422/56 |
| 3,715,192 | 2/1973 | Wenz et al. | 422/56 |
| 4,088,448 | 5/1978 | Lilja et al. | 422/58 X |
| 4,223,089 | 9/1980 | Rothe et al. | 436/165 X |
| 4,254,083 | 3/1981 | Columbus | 436/165 X |
| 4,275,031 | 6/1981 | Fischer et al. | 422/58 X |
| 4,426,451 | 1/1984 | Columbus | 436/165 X |
| 4,582,684 | 4/1986 | Vogel et al. | 422/58 X |
| 4,604,264 | 8/1986 | Rothe et al. | 422/56 |
| 4,678,757 | 7/1987 | Rapkin et al. | 422/58 X |

Primary Examiner—Jill Johnston
Attorney, Agent, or Firm—Reising, Ethington, Barnard, Perry & Milton

[57] ABSTRACT

A reagent test strip (10,10') includes a support medium (12,12') having a handle portion (14,14') and a reagent support portion (16,16'). A reagent (18,18') is fixedly adhered to the reagent support portion (16,16'). A cover (20,20') is mounted on the support medium (12,12') and over the reagent (18,18'). The cover (20,20') defines a capillary chamber (28,28') having two open ends (30,30') and a predetermined volume only over the reagent surface (19) for drawing a predetermined amount of liquid (32,32') into the capillary chamber (28,28') to quantitatively react all of the liquid with the reagent (18,18'). The cover (20,20') is the only structure over the reagent surface (19,19') and is spaced thereover only sufficiently to establish the predetermined volume for acting as a capillary. Methods of using and manufacturing the reagent test strip (10,10') are also disclosed.

25 Claims, 1 Drawing Sheet

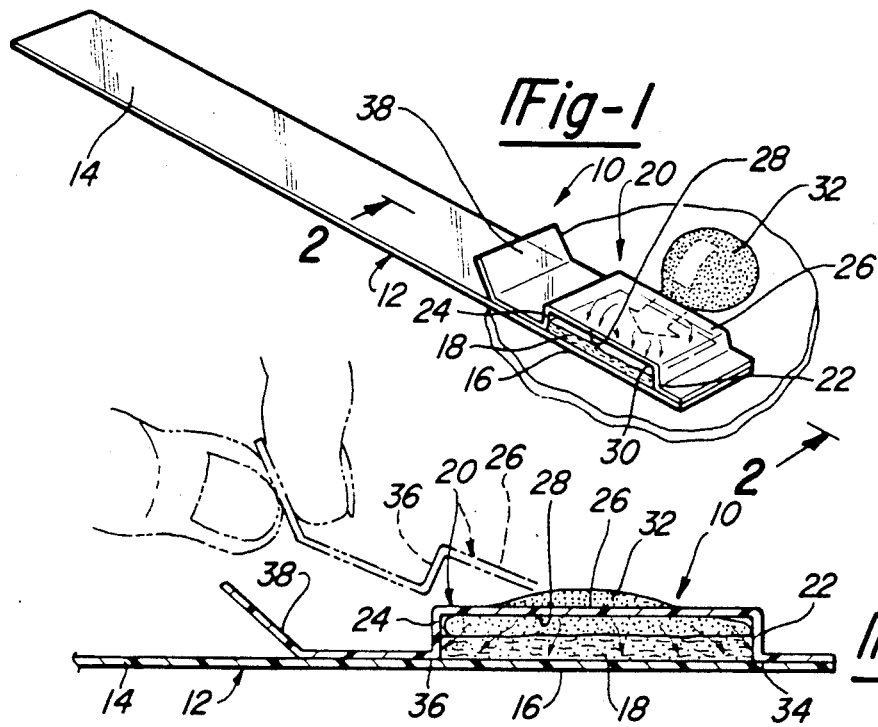
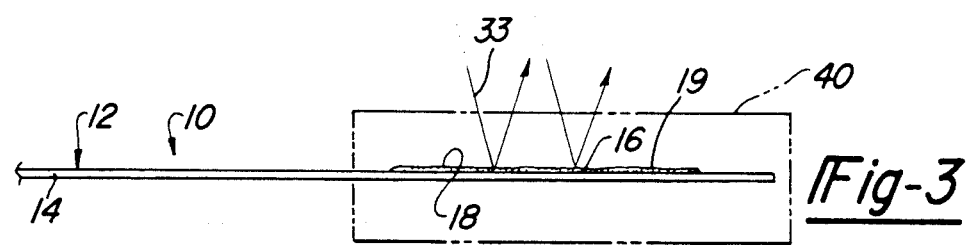
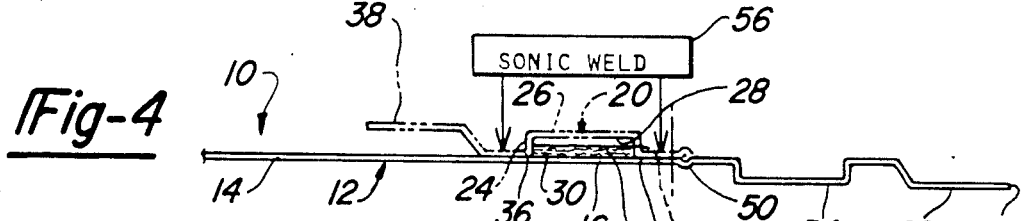
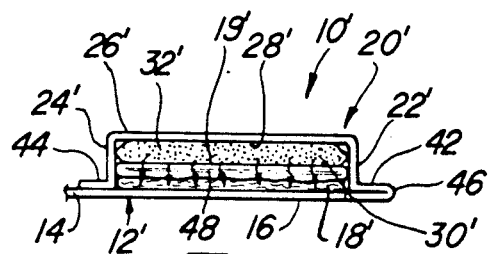
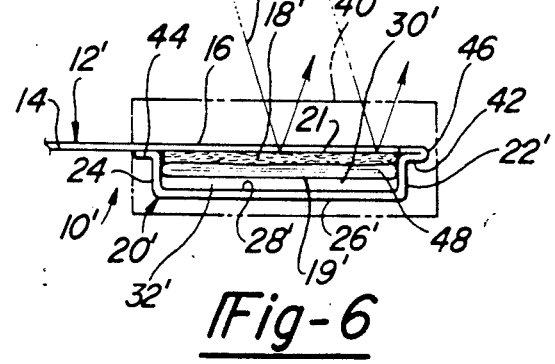

REAGENT TEST STRIP

TECHNICAL FIELD

The present invention relates to reagent test strips, a process for the production thereof, and method of using the same. More specifically, the invention relates to reagent test strips which generally include a plastic support and a reagent or a plurality of reagents disposed thereon for use in home and hospital diagnostic tests, such as glucose monitoring.

BACKGROUND ART

Many home and hospital diagnostic tests, such as glucose monitoring, utilize test strips with a reagent that under goes a colorimetric change upon contact with the glucose containing blood sample. However, commercially available reagent test strips have several limitations.

The patient using a prior art test strip must completely cover the reagent on the strip with a droplet of blood. Since there is no way for the blood to remain on the reagent by adhesion, most of the blood droplet adheres to the finger or other body appendage from which it was obtained by a lancet cut. Incomplete or uneven coverage of the reagent by the blood droplet results in uneven reaction with the reagent. Before the strips can be read, either visually or by a machine, the droplet of blood must be blotted off of the reagent. This often results in residual blood on the reagent if blotting is too gentle or a loss of reagent surface if the blotting is too rigorous. Each of the aforementioned limitations results in nonquantitative determinations. If borderline levels of the reactant are contained in the blood sample, even qualitative determinations can be inaccurate.

The semi-quantitative capability of prior art test strips has been recognized in the prior art. The U.S. Pat. No. 4,604,264 to Rothe et al, issued Aug. 5, 1986 discloses a test strip including a dry reagent containing film layer coating embedded at least preponderantly onto and into only one side of a carrier layer made of a multifilar fabric or fleece. The U.S. Pat. No. 3,715,192 to Wenz et al, issued Feb. 6, 1973 discloses an indicator strip, useful in analytical chemical procedures, which includes a reagent impregnated capillary material having at least a partially transparent film on one side and on the other side a film forming a hollow space which is in communication with the capillary material. The hollow space above the capillary material provides quicker absorption of a liquid material drawn onto a capillary material impregnated with the reagent. The patent states that it is necessary to submerge the end of the test strip including the capillary material and cover thereover into a liquid sample for the capillary material to be immersed in the sample. The main advantage of the construction is to enable the capillary material to absorb the liquid medium to be examined quickly to prevent chromotographic separation of the reagent during the absorption of the liquid media.

U.S. Pat. No. 4,088,484 to Lilja et al, issued May 9, 1978, discloses an apparatus for sampling with a cavity between two planar surfaces. A reagent is contained in the cavity and is dissolved with a sample drawn into the cavity by gravity, vacuum or capillary action. Analysis occurs by transmission of light across the optical path directly through the two planar surfaces. Hence, the amount of spacing between the surfaces must be critically controlled.

A related article entitled "Evaluation of 'Hemo Cue', a New Device for Determining Hemoglobin", *CLINICAL CHEMISTRY*, volume 32, Nov. 3, 1986, discloses a technique based on an optical measuring cuvet of a small volume and short light path. Reagents for lysing red blood cells are deposited on the inner walls of a cuvet cavity and a blood sample is drawn into the cavity by capillary action and mixed with the reagent. An instrument calculates the concentration of hemoglobin in the sample by the amount and color of light transmitted through the optical path containing the sample and displays the results. The "Hemo Cue" ® (registered trademark is owned by Leo Diagnostics AB Helsingborg, Sweden) comprises a pair of plastic plates having a space therebetween and a pointed edge. An area within the plates has the dry reagent deposited thereon. The reagent is mixed with the sample drawn into the space between the plates. Although "Hemo Cue" ® is shown to produce quantitative analysis, a sample is drawn through the communicating passageway and into the reagent containing area which is necessarily larger in volume than that needed for the quantitative measurement.

New lancing devices, such as disclosed in the U.S. patent application Ser. No. 764,051 to Dombrowski, filed Aug. 9, 1985, now U.S. Pat. No. 4,653,513, are capable of making incisions in body parts which are not highly vascularized. The device draws a small sample of blood from the incision. In combination with these devices, it is necessary that a test strip require a small amount of blood to make a quantitative determination, such as a glucose determination.

The present invention addresses the aforementioned limitations of the prior art by completely recovering and obtaining a very small precise volume of blood to evenly and completely cover a reagent surface. The device only draws an amount of blood quantitatively necessary to completely cover the reagent and produce a quantitative colorimetric reaction. The results of the reaction are not determined by light transmitted through a sample-reagent mixture, so the defined optical path length is not required.

SUMMARY OF THE INVENTION

The present invention provides a reagent test strip including a support medium having a handle portion and a reagent support portion. A reagent is fixedly adhered to the reagent support portion. A cover is mounted on the film and only over the reagent, the cover defining capillary chamber means having two open ends and a predetermined volume only over the reagent surface for drawing a predetermined amount of liquid into the capillary chamber means to quantitatively react with the reagent. The cover is the only structure over the reagent surface and is spaced thereover only sufficiently to establish the predetermined volume for acting as a capillary.

The present invention further provides a method of making the reagent test strip including the steps of cutting a predetermined length of a support medium and embossing a first depression having a predetermined length proximate to one end of the support medium and a second depression between the first depression and the aforementioned end of the support medium. A reagent is fixedly adhered to the support medium at a distance from the first depression that is equal to the distance of the second depression from the first depression in the opposite direction. The support medium is folded at the first depression so that the second depression forms a covered chamber having two open sides directly over the reagent. The folded over portion is adhered to the support medium.

The method of making a quantitative analytical determination of a soluble constituent in a liquid sample utilizing the present invention includes the steps of contacting the chamber defined between the reagent surface and the cover with the liquid sample. A known quantity of liquid is drawn into the chamber by capillary action of the chamber and saturates the fixed reagent. The soluble constituent of the liquid is reacted with the reagent to form a reaction product. A quantitative determination is made of the amount of the reaction product by reflectance photometry.

FIGURES IN THE DRAWINGS

Other advantages of the present invention will be readily appreciated as the same becomes better understood by reference to the following detailed description when considered in connection with the accompanying drawings wherein:

FIG. 1 is a perspective view of the present invention drawing an aliquot of blood into the capillary chamber thereof;

FIG. 2 is a cross sectional view taken substantially along lines 2—2 of FIG. 1;

FIG. 3 is a side elevational view of the present invention within a monitoring device;

FIG. 4 shows the subject manufacturing process;

FIG. 5 is a side elevational view of a second embodiment of the present invention; and FIG. 6 is a side elevational view of the second embodiment of the present invention in a monitoring device.

DETAILED DESCRIPTION OF THE INVENTION

A reagent test strip constructed in accordance with the present invention is generally shown at 10 in the drawings. Primed numbers are used to indicate like structures between the several embodiments.

The reagent test strip 10 includes a support medium generally indicated at 12. The support medium 12, includes a handle portion 14 made to be grasped by the user of the test strip. The support medium 12 further includes a reagent support portion 16.

The support medium can be made from various materials already known in the art. For example, the support medium may be made from a suitable thin, flat film of synthetic material conventionally employed previously for such purposes. The films are not porous and must be liquid impermeable. Suitable materials for the films are, for example, polyethylene, polypropylene, polyvinyl-type polymers, or copolymers, such as polyvinyl chloride, polyvinyl acetate, polyvinylidene chloride, or polyethylene glycol terephthalates and the like.

A reagent 18 is adhered to the reagent support portion 16. The reagent 18 has a reagent surface 19. The reagent may comprise the glucose oxidise system and indicator system as disclosed in the U.S. Pat. No. 3,092,465 to Adams et al, issued Jun. 4, 1963 or other detecting reagents for blood or other bodily fluids commonly known presently in the art. The reagent can be adhered by glue or other means which retains the reagent on the support medium and causes the reagent to be insoluble in the tested liquid. The reagent may have its own adhesion capability thereby obviating a need for the glue as long as the reagent remains adhered to the support medium 12 and insoluble in the test liquid. Additionally, although the test strips disclosed herein and constructed in accordance with the present invention are preferably used for the detection of component materials of blood, the strips may be also suitably modified by the choice of reagent for use with other aqueous media, such as urine, saliva, and other aqueous media. Moreover, the present invention may also be utilized for the determination of component materials in other aqueous media, such as drinking water, effluent and the like, and possibly also in organic solvents in which they are insoluble.

A cover, generally indicated at 20, is mounted on the support medium 12. The cover 20 includes side wall portions 22,24 and a ceiling portion 26 extending therebetween. The side wall portions 22,24 are disposed directly adjacent the reagent 18 and the ceiling extends therebetween so as to only cover the reagent surface 19. The cover 20 defines a capillary chamber 28 having two open ends 30 (only one open end 30 being shown in each of the Figures) and a predetermined volume only over the reagent surface 19 for drawing a predetermined amount of liquid 32 into the capillary chamber 28 to quantitatively react with the reagent 18. For example, the ceiling portion 26 may be spaced 0.25 to 1.0 millimeters from the reagent surface 19. The space between the reagent surface 19 and cover 26 is critical. The space between cover 26 and support 16 is variable dependent upon the thickness of the reagent for a particular test. The cover 20 is the only structure over the reagent surface 19 and is spaced therefrom only sufficiently to establish the predetermined volume for acting as a capillary.

By capillary action, the capillary chamber 28 per se draws in a predetermined amount of the liquid 32 to directly and completely cover the reagent surface 19. The capillary chamber 28 obtains a precise amount of liquid sample to evenly and completely cover the reagent surface 19 and saturate the reagent 18. Since the capillary chamber 28 is made to a predetermined size with respect to the amount of reagent 18 adhered to the reagent support portion 16, a quantitative determination of the amount of reactant within the liquid sample is determined. The capillary chamber 18 physically draws the liquid sample completely over the reagent surfact 19 thereby evenly and completely covering the reagent surface 19. No excess liquid is required other than that necessary to cover the reagent surface. The volume of liqud reacting with the reagent 18, which is important in many diagnostic tests, is thereby controlled by the present invention.

As shown in FIGS. 1-3, the cover 20 is removably adhered to the support medium 12. Each of the wall portions 22,24 has an end portion 34,36, respectively, removably adhered to the support medium 12 and perfecting a liquid tight seal therewith. The end portions 34,36 may be adhered to the support medium 12 by means well known in the art, such as by a plastic adhesive or sonic welding. It is a requirement of the adhesive, however, that it perfect a seal so that there is no leakage. Such leakage would result in nonquantitative determinations.

As shown in FIGS. 1 and 2, the cover 20 includes a tab portion 38 extending from one of the end portions 36 adjacent to the support medium 12. The tab portion 38 extends away from and is independent of the support medium 12.

In use, touching of the lateral aspect 30 of the capillary chamber 28 between the cover 20 and reagent 18 to a small droplet of blood 32, as shown in FIG. 1, results in filling of the capillary chamber 28 with blood by capillary action. The capillary action greatly facilitates collection of the blood sample. The volume of blood 32 reacting with the reagent 18 is important in many diagnostic tests, and is controlled by the size of the capillary chamber 28. After incubation, for example 60 seconds for common glucose determination, the cover 20 is grasped by the fingers and removed, as shown by the hatch lines in FIG. 2. The reagent 18 is then blotted of surface blood. The colorimetric reaction can either then be visually determined for a qualitative determination or the reagent 18 is disposed in a commercially available reflectance photometer, such as that shown schematically in FIG. 3 at 40, for a quantitative determination. Once the cover 20 is manually removed, the reagent strip 10 can be read by commercially available reflectance photometers. The reaction is quantitated by a reflective scanning of the reagent surface. Light 33 of specific wavelengths is reflected off of the reagent surface 19. The reagent changes colors and the color change is quantitated by the scanner. Existing reagent strips can be modified as described above.

A second embodiment of the present invention is generally shown at 10' in FIGS. 5 and 6. One of the end portions 42 adjacent the wall 22' is integrally connected to the support medium 12' and the other end 44 of the other end wall 24' is permanently adhered thereto. In this embodiment, the support medium 12' and the cover 20' are an integral member. One end of the support medium 12' has a curved portion 46 interconnecting the integrally connected end portion 42 to the support medium 12'.

As shown in FIGS. 5 and 6, a filter material 48 is disposed over the reagent surface 19' for filtering solid components from the liquid 32' drawn into the capillary chamber 28' prior to the liquid 32' contacting and reacting with the reagent 18'. The filter material 48 can comprise a fibrous material or a polymeric microporous material or any other filtration material known in the art. For example, in performing a glucose determination it is preferable to react the glucose determining reagent a known quantity of blood serum. The filter selectively allows serum to pass through and yet retains the blood cells on its surface. Accordingly, as shown in FIG. 5, the drop of blood 32' fills the chamber 28' covering the membrane filter 48 and only the serum passes through the filter 48 to the reagent 18'.

The polymeric filter 48 can be made very thin, having a thickness of approximately 25 microns and a small pore size, of approximately 5 microns. This membrane is capable of selectively allowing the serum to pass through and yet retains the blood cells on its surface. This embodiment provides for a one step process not requiring removal of the cover or blotting of the reagent surface. Hence, there is less opportunity for operator error or disturbance of the reagent 18'. The quantitive results are obtained by reflectance of light 33 off of the reagent 18' through the clear support member 16.

The present invention further provides a method of making the reagent test strip 10.

Referring to FIG. 4, generally, a support medium 12 is cut to a predetermined length. A first depression 50 is embossed at a predetermined distance approximate to one end 52 of the support medium 12. Depression 50 forms a structural hinge. A second depression 54 is embossed between the first depression 50 and the end 52 of the support medium 12. The reagent 18 is deposited on the support medium 12 at a distance from the first depression 50 that is equal to the distance of the second depression 54 from the first depression 50 in the opposite direction. The support medium 12 is folded over at the first depression 50 so that the first depression 50 acts as a hinge and the second depression 54 forms the covered chamber 28 having the open sides 30 over the reagent 18. The folded over portion is then adhered to the support medium 12.

More specifically, the step of adhering the folded over portion or cover 20 to the support medium 12 may be accomplished by depositing an adhesive on the support medium 12 adjacent to each end of the reagent 18 and the cover 20 is forced into contact with the adhesive. Alternatively, as shown in FIG. 4, a sonic welding device, as schematically shown at 56, may be utilized to weld the side walls 22,24 to the support medium 12.

The first depression 50 forms a U-shaped fold or hinge between the cover 20 and the remainder of the support medium 12. To form the embodiment shown in FIGS. 1–3, the U-shaped fold is sheared off after the cover 20 is adhered to the remainder of the support medium 12. Hence, the entire cover 20 can be removed from the support medium 12.

The method further includes the step of embossing the end portion 60 of the support medium 12 adjacent to the second embossment 54 whereby folding over of the support medium 12 at the first embossment or hinge 50 forms the chamber 28 from the second embossment 54 and the tab 38 spaced from the remainder of the support medium 12 from the embossed end 60.

The invention has been described in an illustrative manner, and it is to be understood that the terminology which has been used is intended to be in the nature of words of description rather than limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A reagent test strip (10,10') comprising a support medium (12,12') including a handle portion (14,14') and a reagent support portion (16,16'); an insoluble reagent (18,18') fixedly adhered to said reagent support portion (16,16') defining a reagent surface (19,19') capable of quantitatively changing reflectance in the presence of a reactant to be quantitatively determined; and a cover (20,20') mounted on said support medium (12,12') and only over said reagent (18,18'), said cover (20,20') defining capillary chamber means (28,28') having two open ends (30,30') and a predetermined volume only over said reagent surface (19,19') for drawing a predetermined amount of liquid (32,32') into said capillary chamber means (28,28') and only over said reagent surface (19,19') to quantitatively react all of the liquid with said reagent (18,18') and quantitatively change the reflectance of the reagent surface, said cover (20,20') being the only structure over said reagent surface (19,19') and being spaced thereover only sufficiently to establish said predetermined volume for acting as a capillary.

2. A test strip as set forth in claim 1 wherein said cover (20) is removably adhered to said support medium (12).

3. A test strip as set forth in claim 2 including tab means for being gripped to remove said cover (20) from said support medium.

4. A test strip as set forth in claim 3 wherein said cover (20,20') includes two spaced upstanding wall portions (22,22',24,24') adjacent opposite ends of said reagent (18,18') defining closed ends of said capillary chamber means (28,28') and a ceiling portion (26,26') extending therebetween.

5. A test strip as set forth in claim 4 wherein each of said wall portions (22,24) have an end portion (34,36) removably adhered to said support medium (12) and perfecting a seal therebetween.

6. A test strip as set forth in claim 5 wherein said tab means includes a tab portion (38) extending from one of said end portions (36) adjacent to said support medium (12), said tab portion (38) being independent of said support medium (12).

7. A test strip as set forth in claim 6 wherein said tab portions (38) are spaced from said support medium (12).

8. A test strip as set forth in claim 1 wherein said cover (20,20) includes two spaced upstanding wall portions (22,22',24,24') adjacent opposite ends of said reagent (18,18') defining closed ends of said capillary chamber means (28,28') and a ceiling portion (26,26') extending therebetween.

9. A test strip as set forth in claim 8 wherein each of said wall portions (22,24) includes an end portion (42,44), one of said end portions (42) being integrally connected to said support medium (12'), said other end portion (44) being fixedly adhered to said support medium (12').

10. A test strip as set forth in claim 8 wherein said cover (20,20') is an optically clear material.

11. A test strip as set forth in claim 1 wherein said support medium (12) comprises a thin and flat polymeric film.

12. A test strip as set forth in claim 1 wherein said capillary chamber (28) has a height from said reagent surface (19,19') to said cover (20) of 0.25 to 1.00 millimeters.

13. A test strip as set forth in claim 1 wherein said support medium (12,12') is an optically clear material.

14. A test strip as set forth in claim 1 including filter means (48) disposed over said reagent (18') for filtering solid components from the liquid (32') drawn into said capillary chamber means (28') prior to the liquid (32') contacting and reacting with said reagent (18').

15. A test strip as set forth in claim 14 wherein said filter means (48) includes a fibrous material.

16. A test strip as set forth in claim 14 wherein said filter means (48) includes a polymeric microporous material.

17. A method of making a reagent test strip (10,10') including the steps of: cutting a predetermined length of a support medium (12); embossing a first depression (50) at a predetermined distance proximate to one end (52) of the support medium (12) and a second depression (54) between the first depression and the end (52) of the support medium (12); fixedly adhering an insoluble reagent (18) on the support medium (12) at a distance from the first depression (50) that is equal to the distance of the second depression (54) from the first depression (50) in the opposite direction; folding over the support medium at the first depression (50) so that the second depression (50) forms a covered chamber (28) directly over the reagent (18) with two open sides; and adhering the folded over portion to the support medium (12).

18. A method as set forth in claim 17 wherein the step of adhering the cover (20) to the support medium (12) is further defined as depositing an adhesive on the support medium (12) adjacent each end of the reagent (18) and forcing the folded over portion into contact with the adhesive.

19. A method as set forth in claim 18 wherein the first depression (50) forms a U-shaped fold between the cover (20) and the remainder of the support medium (12), the method further including the step of shearing off the U-shaped fold after the cover (20) is adhered to the remainder of the support medium (12).

20. A method as set forth in claim 17 further including the step of embossing the end (60) of the support medium (12) adjacent to the second embossment (54) whereby folding over of the support medium (12) at the first embossment (50) forms the covered chamber (28) from the second embossment (54) and a tab (38) spaced from the remainder of the support medium (12) from the embossed end (60).

21. A method of making a quantitative analytical determination of a soluble constituent in a liquid sample (32,32') comprising the steps of: contacting a lateral open aspect of a chamber (28,28') with a liquid (32,32') wherein the chamber (28,28') is defined between a reagent surface (19,19') of an insoluble reagent (18,18') fixedly deposited thereon and a cover (20,20'); drawing a known quantity of the liquid (32,32') into the chamber (28,28') by capillary action of the chamber (28,28') to only cover the reagent surface (19,19'); saturating the reagent (18,18') with the liquid while completely reacting a soluble constituent of the liquid (32,32') with the reagent (18,18') to form a reaction product on the reagent surface (19,19'); and reflecting a light beam (33) off of the reagent (18,18') to quantitatively determine the amount of the reaction product by reflectance photometry.

22. A method as set forth in claim 21 further including the steps of removing the cover (20) and removing the liquid (32) from the reagent surface (19,19') and reflecting the light beam (33) off of the blotted reagent surface (19,19').

23. A method as set forth in claim 21 wherein the liquid (32,32') is whole blood, said method further including the steps of lancing the skin, drawing blood (32,32') out from the lanced skin, and contacting the chamber (28,28') with the drawn blood (32,32').

24. A method as set forth in claim 23 further including the step of separating the serum from the whole blood in the chamber (28') and reacting the serum with the reagent (18').

25. A method as set forth in claim 24 wherein the support medium (12,12') is a clear material, the determining step being further defined as photometrically determining the amount of reaction product by reflecting the light beam (33) against the reagent surface (19,19') through the clear support medium (12,12') whereby it is not necessary to remove the liquid from the reagent surface.

* * * * *